United States Patent [19]

Khanna et al.

[11] Patent Number: 4,973,549

[45] Date of Patent: Nov. 27, 1990

[54] QUANTITATIVE DIAGNOSTIC ASSAY EMPLOYING SIGNAL PRODUCING AGENT BOUND TO SUPPORT AND MEASURING MIGRATION DISTANCE OF DETECTABLE SIGNAL

[75] Inventors: Pyare Khanna, Fremont; Prithipal Singh, Los Altos Hills, both of Calif.

[73] Assignee: Chemtrak Corporation, Sunnyvale, Calif.

[21] Appl. No.: 64,883

[22] Filed: Jun. 22, 1987

[51] Int. Cl.$^5$ ............................................. C12Q 1/60
[52] U.S. Cl. ...................................... 435/11; 435/14; 435/25; 435/28; 435/805; 436/518; 436/536; 436/807; 436/810; 436/904; 422/56; 422/57; 422/59; 422/61; 422/70; 422/82.05
[58] Field of Search ..................... 435/11, 14, 25, 28, 435/805; 436/518, 536, 807, 810, 904; 422/56, 59, 61, 68, 70, 57

[56] References Cited

U.S. PATENT DOCUMENTS

| | | | |
|---|---|---|---|
| 3,620,677 | 11/1971 | Morison | 422/56 |
| 3,891,507 | 6/1975 | Breuer | 435/14 |
| 4,046,514 | 9/1977 | Johnston et al. | 435/14 |
| 4,059,407 | 11/1977 | Hochstrasser | 435/14 |
| 4,248,973 | 2/1981 | Kallies | 435/805 X |
| 4,252,903 | 2/1981 | Kallies | 422/56 X |
| 4,281,062 | 7/1981 | Kallies | 435/14 |
| 4,298,688 | 11/1981 | Kallies | 435/14 |
| 4,366,241 | 12/1982 | Tom et al. | 422/56 X |
| 4,435,504 | 3/1984 | Zuk et al. | 422/56 X |
| 4,447,527 | 5/1984 | Monte et al. | 436/536 X |
| 4,654,310 | 3/1987 | Ly | 435/805 X |
| 4,772,561 | 9/1988 | Genshaw | 435/14 X |

*Primary Examiner*—Esther L. Kepplinger
*Assistant Examiner*—Carol A. Spiegel
*Attorney, Agent, or Firm*—Bertram I. Rowland

[57] ABSTRACT

Methods and kits are provided for detecting analytes, which can be measured directly or indirectly, by production of an enzymatic product. The enzymatic product reacts with a signal producing reagent bound to a bibulous strip. Various devices are employed for producing a reaction, directly or indirectly, with the analyte and then providing for migration of the product through the bibulous strip with reaction with the reagent to produce a detectable signal. The distance from a pre-determined site to the border of the detectable signal is a quantitative measure of the analyte in the sample.

3 Claims, 2 Drawing Sheets

QUANTITATIVE DIAGNOSTIC ASSAY EMPLOYING SIGNAL PRODUCING AGENT BOUND TO SUPPORT AND MEASURING MIGRATION DISTANCE OF DETECTABLE SIGNAL

INTRODUCTION

1. Technical Field

Diagnostic assays for analytes which result, directly or indirectly, in a substrate for an enzyme.

2. Background

There are many analytes present in physiological fluids which are desirably monitored in a doctor's office or in the home. Particularly, where untrained individuals are required to carry out diagnostic assays for quantitative results, the protocols and equipment should be relatively simple. The equipment should be easily manipulated and not subject to deterioration, injury, or other change which may affect the result. The protocol should have the fewest number of steps, as well as a minimal number of measurements. The fewer steps and measurements, the less likely for error to be introduced by the person performing the assay.

Because of the need for individuals to measure a number of different analytes, there has been substantial attention to producing protocols and equipment which can be afforded by an individual and are relatively foolproof. In many cases, however, the assay requires electronic equipment to quantitate the result, which results in a significant expenditure by the user. Also, some of the techniques require a number of steps and measurements, which are found to introduce significant errors into the results. There is, therefore, a continuing need for alternative techniques for rapid measurement of analytes by untrained individuals.

3. Relevant Literature

U.S. Pat. Nos. 4,168,146; 4,298,688; 4,299,916; 4,361,537; 4,366,241; 4,435,504; 4,442,204; 4,533,629; 4,446,232; 4,447,526 and 4,454,094 as exemplary of various stick and strip assays. Sloan et al., *Clin. Chem.* (1984) 30:1705–1707: and Virapen and Harding, *Clin. Chem.* (1985) 31:925, describe a stick assay for chloride.

SUMMARY OF THE INVENTION

Novel devices are provided which include a non-diffusively bound detectable reagent bound to a bibulous support. The device is employed in conjunction with a reagent composition which includes at least one enzyme, conveniently as a mixture of enzymes, which reacts directly or indirectly with an analyte to produce a product, which product reacts, directly or indirectly, with the bound reagent to produce a detectable signal. The measured distance from a predetermined point to a point where signal is no longer readily observed is a quantitative measure of the analyte.

DESCRIPTION OF THE SPECIFIC EMBODIMENTS

Figure 1:
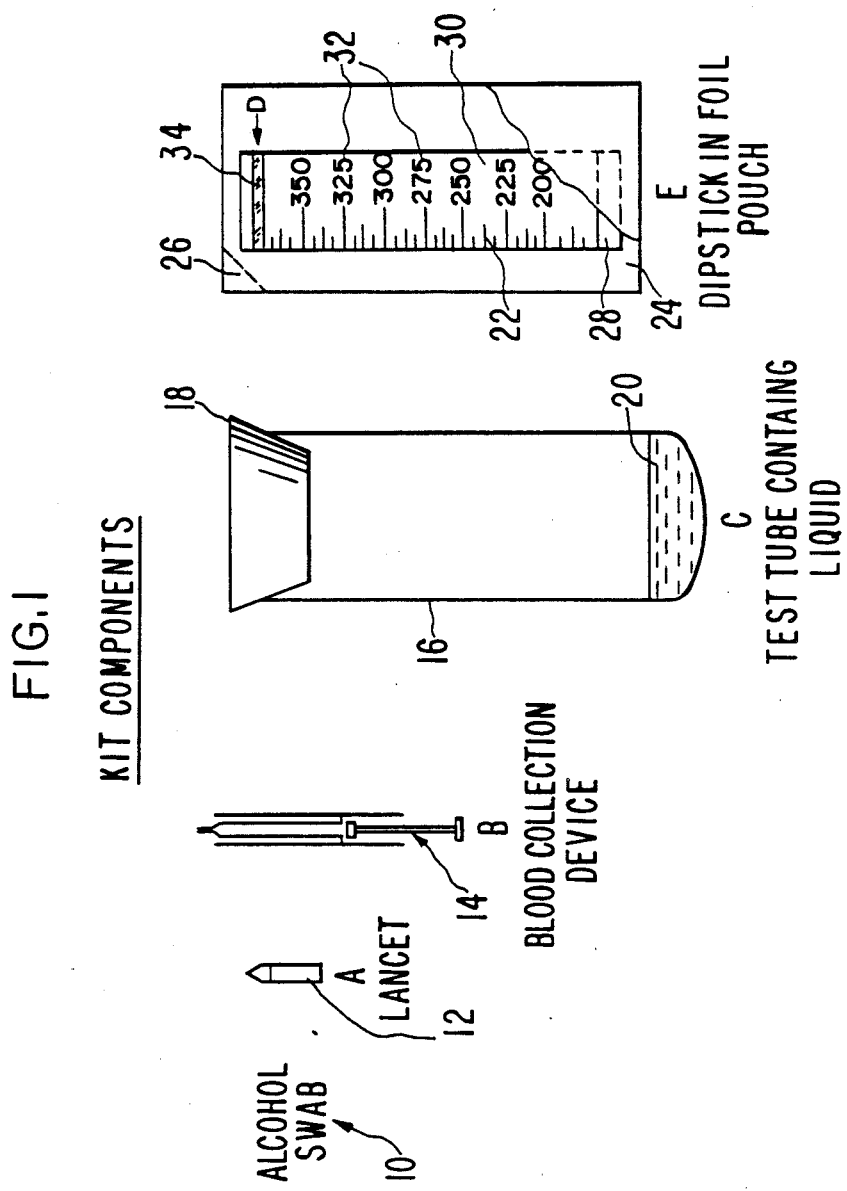
FIG. 1 is a cartoon of components of a kit in accordance with the subject invention.

Methods and kits are provided for detecting analytes which are, directly or indirectly, substrates of enzymes, resulting in a product which by a catalyzed or uncatalyzed reaction may react with a reagent nondiffusively bound to a support to produce a detectable signal. The method involves combining the sample with an enzyme composition, where the enzyme composition includes any additional substrates required for reaction with the analyte. Where the enzyme product does not react at a desired rate with the bound reagent, additional components may be included in the enzyme reaction mixture, on the support or in the developer solution, to enhance the rate of reaction between the enzyme product and the bound reagent.

The subject invention may be employed with any analyte which can react with an enzyme or product of an enzyme to produce a product which may react, directly or indirectly, with a reagent to produce a detectable signal. The reaction with the reagent may be catalyzed or uncatalyzed, particularly enzyme catalyzed. Various analytes may be used, particularly alkanols, such as glucose, cholesterol, ethanol, etc. Other compounds which may be analyzed include urea, NAD(P)-/NAD(P)H, FAD/FADH, FMN/FMNH, etc. where the cofactors may be coupled to other analytes to provide the desired result. See U.S. Pat. Nos. 4,134,792 and 4,374,925 for a description of enzyme systems. For the most part the enzymes will be oxidoreductases. The concentration range of the various analytes will vary depending upon the analyte. Therefore, the concentration of the enzyme reaction components will relate to the nature of the analyte and the concentration range of the analyte of interest.

The enzyme reaction composition will involve the enzyme which reacts, directly or indirectly, with the analyte and any additional cofactors or substrates necessary to produce the product which reacts with the reagent. For example, where the analyte is a cholesteryl ester, the enzyme reaction mixture will include a cholesterol esterase and cholesterol oxidase. The product of this reaction is hydrogen peroxide. Depending upon the bound reagent, the mixture may also include peroxidase, which will serve to catalyze the reaction between the hydrogen peroxide and the bound reagent, which in this case may be a leuco dye. For glucose, one may employ glucose oxidase in place of the cholesterol oxidase, while for L- or D-amino acids one may employ amino acid oxidase in place of the cholesterol oxidase. These enzymes all employ oxygen as the hydrogen recipient in the oxidation, so as to produce hydrogen peroxide. Thus, any analyte which, directly or indirectly, can be coupled with an enzyme reaction to produce hydrogen peroxide, can be employed in the subject invention.

Other systems which may be employed with the same or other analytes and other enzymes include hexokinase and glucose-6-phosphate dehydrogenase with glucose and the reagent N-nitrophenylformazan, lactate dehydrogenase hydrogenase with lactate and the reagent methyltetrazole, alcohol dehydrogenase with ethanol and the reagent trichlorophenolindophenol, etc. See particularly, U.S. Pat. No. 4,374,925, cols. 25–30.

Various devices may be employed which involve a bibulous strip to which is non-diffusively bound a reagent capable of providing a detectable signal. For the most part, the reagents will be leuco dyes, which are stable under ambient conditions, but upon reaction with an oxidant or reductant result in production of a detectable color. While the opposite situation is possible, a colored dye which is bleached, preferably a leuco dye, will be employed as the reagent.

The bibulous strip may be prepared from a wide variety of materials which allow for capillary movement of a liquid, particularly an aqueous liquid. Various materials include cellulosic materials, such as paper, nitrocellulose, silica, alumina, glass fibers, or the like. No chromatography is necessary, rather the significant factor is that the reagent be conveniently bound to the support, the support does not interfere with the production of a detectable signal, and desirably the support allows for a clear distinction between the region having the detectable signal and the region from which the detectable signal is absent. The particular material employed as the bibulous strip is not critical to this invention, but conveniently paper will be employed.

The device may assume various structures. In one aspect, the device may be a simple dipstick which is calibrated, so that the region delineating between the developed detectable signal and the absence of the signal can be read from a scale printed on the device. While it will usually be desirable that the markings be affixed to the device, by the term calibrated is intended that the reagent is distributed in a predetermined manner to provide a scale related to analyte concentration. The strip may be linear, having one dimension substantially larger than the other dimension, circular, or may have a reaction pad supported by a circular or linear strip. Alternatively, a capillary may be employed filled with a bibulous material, where the filler of the capillary acts as a support for the detectable reagent.

The thickness of the bibulous support will generally be from about 5 to 50 mil and, depending upon the nature of the support, may have an inert backing. Various inert backings may be employed, such as Mylar ®, polyvinyl chloride, polyethylene, etc. The strips will generally be at least 1 mm wide, usually at least 2 mm wide, and generally at least about 2 cm long, more usually at least about 3 cm and not more than about 10 cm long. The disks will generally be at least about 1 cm in diameter, and not more than about 5 cm in diameter The capillaries will generally be at least about 0.2 mm and not more than about 2 mm in diameter, generally being about 2 cm long, usually not more than about 10 cm long.

The detectable signal reagent may be bound to the bibulous support in a variety of ways. For some reagents, the reagent may be bound non-covalently, due to adsorption, with or without the aid of heat, usually not above about 60° C. Heating may take from about 5 minutes to about 6 hours. If the signal reagent is physically absorbed, the resulting colored product should also remain bound and not diffuse from its original site. Alternatively, a variety of supports may be activated, so as to provide for active functional groups, which will react with a functional group present on the reagent. The functional groups present on the reagent may be alcohols, mercaptans, amines, or the like.

Various supports may be activated using cyanogen bromide, particularly supports having hydroxyl groups, spacer or linker arms may be provided, where carboxyl or amino groups may be joined to the support, functionalized alkylsilyl groups may be employed, where the functionality may be amino, carboxy, or the like, or aryl groups may be covalently bonded to the support, where the aryl groups may be functionalized with halomethyl, e.g. chloromethyl, amino, which may be diazotized if desired, or the like. These various functionalities may be joined to the reagent, either directly where the reagent has a convenient functional group, where linking does not adversely affect the properties providing the detectable signal, or a bi-functional linking group may be employed, to join the reagent to the support.

The reagent may be applied to the support in a variety of ways, by itself, by itself covalently bonded to a linking group, jointly with the linking group, or the like. The concentration of the reagent in a solution applied to the support will generally be from about 0.01 to 5 mg/ml, more usually from about 0.05 to 2 mg/ml and will depend on the concentration range of interest of the analyte being determined. Various volatile solvents may be used such as water, methanol, ethanol, acetone, etc. and combinations thereof.

The reagent may be applied to the support in a variety of ways, such as spraying, dipping, rolling, or the like. While normally the reagent should be uniformly distributed, in some instances it may be desirable to have a non-uniform distribution, for example, being less concentrated in the region where the lower anayte concentration is measured.

Various compounds may serve as the reagent. With hydrogen peroxide, convenient reagents include tetramethylbenzidine, 1-chloro-4-naphthol, ABTS 2, 2'-azinobis (3-ethylbenzothiazoline-6-sulfonic acid), diammonium salt, dicarboxidine, etc. For other enzyme products, such as ammonia, reagents which may find use include bromocresol green.

The enzymatic reaction mixture will include as already indicated, the appropriate enzymes and any additional cofactors, substrates, or other additives necessary to provide a reaction with the analyte and to produce a product under conditions where the product will react with the bound reagent to produce a detectable signal. The concentration of the various components of the enzymatic reaction mixture will vary widely, depending upon the particular enzyme, the activity of the enzyme, the concentration range of interest of the analyte, and the like. For cholesterol, the concentration of the cholesterol esterase and cholesterol oxidase will generally be in excess and range from about 0.1 to 100 IU(international units) each, more usually from about 0.5 to 10 IU each. For glucose, the glucose oxidase concentration will generally range from about 0.1 to 100 IU, more usually from about 0.5 to 10 IU.

Sufficient substrates and cofactors will be provided, so as not to be rate limiting. Generally, the concentration of the individual component will not exceed about 1 molar, usually not exceeding about 0.5 molar.

Buffers will normally be present to provide a buffered solution having a pH in the range of about 6 to 10, usually about 6.5 to 9, generally being at concentrations of about 50 to 500 mmol. Various buffers may be employed, such as Tris, phosphate, carbonate, MOPS (4-morpholinepropanesulfonic acid), or the like. The particular buffer will be chosen in accordance with the enzyme, so as to minimize any adverse affect of the buffer. Other additives which may be included are salt to provide the desired ionic strength, stabilizers, biocides, and the like. In addition, excipients may be provided to bulk the mixture. For the most part, the mixes will be provided as dry powders, particularly lyophilized powders, following conventional lyophilization techniques. See, for example, U.S. Pat. No. 4,447,527.

Instead of having the enzymatic reaction mixture present as a powder, in some instances it may be desirable to provide for the enzymatic reaction mixture in whole, or in part, non-diffusively bound to a support. The support may be a region of the device, where the region may be in the same sheet or as a separate layer allowing for capillary transport from the layer to the remaining portion of the device. In this situation, it will usually be desirable to provide that the sample is contacted with the region containing the enzymatic reaction mixture, so that the reaction may occur at one site, followed by migration of the product through the measuring region containing the reagent providing the detectable signal. With the hydrogen peroxide producing oxidases, all that will be required is having the enzyme bound to the surface at a site outside the measuring region. The amount of enzyme bound to the surface is not critical, so long as the reaction with the analyte proceeds rapidly and substantially to completion. Various means for binding enzymes to a bibulous surface are known, many of the means employed for binding the leuco dye are available for the enzyme.

Where blood is used or other medium which contains particles, such as cells, which cells may interfere with the assay, it may be desirable to separate the particles before carrying out the assay. With blood, this can be achieved using a membrane, which may be removed from the site at which the sample was placed, or be wiped clean, removing the cells or other particles from the assay device. Alternatively, the blood sample may be hemolysed, or agglutinated with reagents such as wheat germ agglutinin or anti-red blood cell antibody.

In carrying out the assay, different protocols will be employed, depending upon whether the enzymatic reaction mixture is available as a separate mixture or is bound to a support in liquid transport relation to the measuring unit.

The sample may be any physiological fluid, such as urine, blood, plasma, serum, or a processing fluid, or the like. Before use in the assay, the sample may be subject to various treatments, such as dilution in a buffered medium, centrifugation, extraction, concentration, chromatography, etc. The particular manner in which the sample is treated is not critical to this invention, and will depend upon the nature of the sample. As already indicated, with blood, a cell separating membrane can be provided which allows for retention of the cells and passage of the plasma through the membrane into the assay device.

For further understanding of the invention, the figures will now be considered. In FIG. 1, components of the kit are depicted diagrammatically. The kit would contain an alcohol swab 10 and a lancet (A) 12, where the device is to be used for blood analysis. The patient would prick a finger or earlobe with the lancet drawing a drop of blood. A plastic syringe 14 would be provided which would draw up the blood, so as to allow the patient to measure the volume of blood drawn. A test tube (C) 16 has a stopper 18 and the enzymatic chemical reagents 20 at the bottom. The stopper is removed and the blood may be added. Where the reagents are provided as a lyophilized powder, water may be added to dissolve the reagents prior to addition of the sample. Within limits, the amount of liquid added is not critical, since the subject invention is not concentration sensitive, but only sensitive to the absolute amount of the product which is produced. Thus, the amount of liquid to be added can be indicated roughly by an indexing mark on the test tube, not shown, so that the patient may add a sufficient amount of water to assure the dissolution of all of the enzymatic reaction components.

The dipstick (E) 22 is provided in a pouch 24 having serrated rip corner 26 for opening the pouch to remove the dipstick 22. The dipstick 22 has a region 28 at one end for dipping into the solution, which region is not calibrated. The region also can provide for a membrane which prevents cells from passing past region 28 into the calibrated region 30. The calibrated region 30 has a number of calibration lines 32, as indicated, so as to allow for measurement of the height at which a signal can be detected. Band 34 at the end opposite region 28 and indicated with the letter D has a dye, which becomes visual upon being wetted with the eluting solution. The liquid in test tube 16 is allowed to wick up to band D and then the dipstick 22 is removed from the assay solution. One may then directly read the amount of analyte in the sample as a result of the height at which the signal can be detected.

Figure 2A:
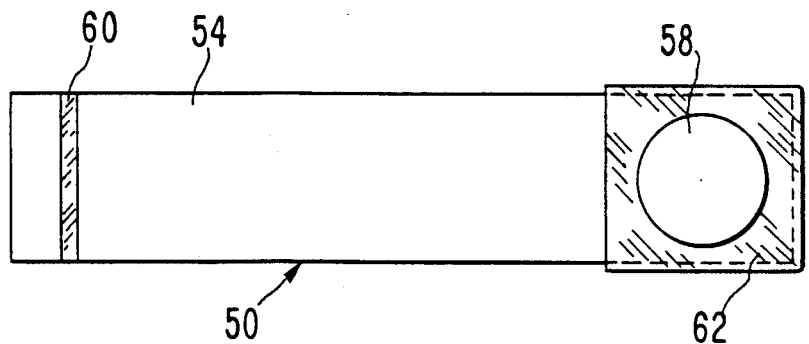
FIGS. 2a and b is an alternative embodiment employing a pad mounted on a strip in side and plan view respectively.
Figure 2B:
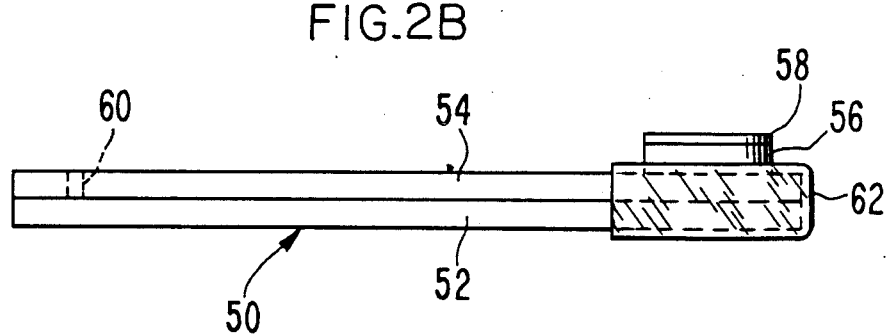

In FIGS. 2a and b is indicated an alternative embodiment as a side view and a plan view. The device 50 has an inert backing 52 and a bibulous strip 54, to which is bound the detectable reagent. In liquid communication with the bibulous strip 54 is pad 56. Bound to pad 56 are the enzyme reaction components, which serve to react with the analyte, either directly or indirectly, to produce a product which reacts with the signal producing reagent. On top of pad 56 is membrane 58 which serves to remove any cells or other particles from the sample, and after having served as a filtration device, may be removed from pad 56 prior to further use of device 50. As with the previous dipstick 22, a band 60 is provided to indicate when the assay may be stopped.

In carrying out the assay, a kit would be provided similar to the kit previously described. However, to perform this assay, one would place the blood drop on top of membrane 58 and allow it to soak into pad 56. The membrane would then be wiped free of red blood cells and the device 50 would then be partially immersed in a solution containing the remaining members of the enzymatic reaction mixture. For example, if one were detecting cholesterol, the pad would be impregnated with cholesterol esterase and cholesterol oxidase, while the development solution would have a peroxidase in order to produce the reaction between the dye impregnated on bibulous layer 54 and the hydrogen peroxide. An inert protective barrier 62 is provided, to ensure that the developing solution passes solely through pad 56. While it is not necessary that the solution solely pass through pad 56, it is preferable that the product not be unduly diluted as it passes through the bibulous strip 54.

For the most part, the developer solution will also include the various agents indicated previously for the enzyme reaction mixture, such as buffer, stabilizers, anti-foaming agents, and the like.

The following examples are offered by way of illustration and not by way of limitation.

EXPERIMENTAL

Reagents

Glucose, cholesterol (200 mg/dl. aq. standard) 4-Cl-1-naphthol, glucose oxidase (GO), cholesterol oxidase, and horseradish peroxidase were purchased from Sigma Chemical Co. Whatman filter paper #541 was purchased from VWR Scientific Supplies. Tris buffer was 55 nM Tris, 0.1 mll/ Triton X-100 ®, pH 8.0.

Immobilization of 4-Cl-1-naphthol On Filter Paper #541

4-Cl-1-naphthol (20 mg) in 10 ml ethanol was diluted with 25 ml Tris buffer and the filter paper soaked in the solution with gentle agitation. After 10 min, the paper was removed, air dried and cut into 6 cm×0.4 cm strips. The strips were stored in a stoppered bottle in the dark until used.

Assay for Hydrogen Peroxide Standards

Stock solutions of hydrogen peroxide (0.05, 0.025, 0.02, 0.005, 0.0025%) were prepared and ~300 µl aliquots transferred to disposable microcuvets. To each microcuvet was added 1 drop of 1:10 diluted horseradish peroxidase (HRP) ~7 IU and the solutions mixed with gentle tapping. Paper strips were dipped to a depth of about 0.25 cm while maintained vertical. After wicking was complete, the strips were removed and the heights of the developed color measured. A linear curve was achieved with a sensitivity of at least $7 \times 10^{-6}$ M $H_2O_2$.

Assay for Glucose

One hundred mg of glucose was dissolved in 10 ml Tris buffer and diluted sequentially with Tris buffer to provide six solutions ranging from 10 to 0.25 mg/ml (50 to 1.4 µM). Aliquots of about 240 µL where transferred to microcuvets and 30 µl each of GO and HRP solutions added with gentle agitation. Individual strips were immersed in the solutions as previously described and wicking allowed to proceed until completion. The height of the blue color was then measured. A standard curve was obtained which was linear between $1.4$–$5.6 \times 10^{-6}$ M glucose.

By varying the 4-Cl-1-naphthol concentration on the strip the sensitivity could be varied. Strips were prepared as previously described using different 4-Cl-1-naphthol concentrations. Standard curves were obtained using the glucose solutions described previously. The slopes obtained are as follows

| 4-Cl-1-Naphthol Conc., mg/ml* | Slope of Standard Curve |
|---|---|
| 0.57 | 1.0 |
| 0.29 | 0.94 |
| 0.14 | 0.70 |

*ethanol-water (1:25 V/V)

It is evident from the above results, that the subject invention provides for a simple rapid protocol having few steps and a minimal number of measurements. The protocol is relatively technician independent, requiring only the measurement of the sample, all of the other aspects of the assay being substantially free of error due to user mistakes. By having an optimized amount of reagent bound to the support and employing reactions which occur rapidly and efficiently, long pathways for development of the signal are avoided, so that one obtains a relatively sharp demarcation line to provide an accurate reading. The kit is very simple, can be readily produced in a reproducible manner, and can be used in the home or doctor's office, without trained technicians necessary to perform the assay. The reading does not require expensive equipment so that it can be performed anywhere, without requiring the user to carry the equipment with them where the user may be traveling. A number of assays can be provided in a single kit, since the test tube is readily reusable, individual pouches require very little space, and reagent refills may be provided in appropriate pouches.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for determining total cholesterol present in a blood or serum sample as cholesterol or cholesterol esters, employing a reagent system which reacts with said cholesterol and cholesterol esters to produce hydrogen peroxide which reacts with a chromogen reagent produce a detectable signal, and employing a bibulous support comprising a calibrated measurement zone to which said chromogen reagent is bound, said method comprising:

contacting at an assay mixture receiving site on said support an assay mixture comprising a sample suspected of containing said cholesterol and cholesterol esters in a liquid medium and an enzyme reaction system comprising cholesterol esterase and cholesterol oxidase whereby said sample and said enzyme reaction system react substantially to completion to produce said hydrogen peroxide;

dipping one end of said bibulous support distant from said measurement zone into a solution comprising horseradish peroxidase, whereby said solution migrates through said assay mixture receiving site into said measurement zone whereby said hydrogen peroxide reacts with said chromogen to produce a detectable signal; and measuring in said calibrated measurement zone the furthest distance from said receiving site of the detectable signal as a measure of the amount of total cholesterol in said sample.

2. A method according to claim 1 wherein said chromogen is 4-chloro-1-naphthol.

3. A method according to claim 2 wherein said assay mixture receiving site is proximal to said one end of said bibulous support.

* * * * *